United States Patent
Veneklasen (10) Patent No.: US 6,541,770 B1
(45) Date of Patent: Apr. 1, 2003

(54) CHARGED PARTICLE SYSTEM ERROR DIAGNOSIS

(75) Inventor: Lee H. Veneklasen, Castro Valley, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/639,141

(22) Filed: Aug. 15, 2000

(51) Int. Cl.⁷ .......................... G01N 23/00; G21K 7/00; H01L 23/58
(52) U.S. Cl. .......................... 250/310; 250/311; 257/48
(58) Field of Search ................................. 250/398, 310, 250/311, 396 ML; 257/48

(56) References Cited

U.S. PATENT DOCUMENTS

| | | | | |
|---|---|---|---|---|
| 3,811,069 A | * | 5/1974 | O'Keeffe | 250/397 |
| 4,475,811 A | * | 10/1984 | Brunner | 283/115 |
| 4,538,105 A | * | 8/1985 | Ausschnitt | 324/716 |
| 4,891,524 A | * | 1/1990 | Yasuda et al. | 250/398 |
| 5,674,650 A | * | 10/1997 | Dirksen et al. | 356/401 |
| 5,751,004 A | * | 5/1998 | Robinson et al. | 250/492.2 |
| 5,831,273 A | | 11/1998 | Someda et al. | |
| 5,936,252 A | * | 8/1999 | Stickel et al. | 250/491.1 |
| 6,194,732 B1 | | 2/2001 | Okino | |

FOREIGN PATENT DOCUMENTS

EP    0669636 A1    8/1995

* cited by examiner

Primary Examiner—Jack Berman
Assistant Examiner—Kalimah Fernandez
(74) Attorney, Agent, or Firm—Jung-hua Kuo (57) ABSTRACT

A plurality of features are first formed on a workpiece in a special standard test pattern, and these features are then overwritten with a charged particle beam in an overlay pattern which matches the standard pattern such that the overlay regions overlap edges of the features in the standard pattern. A backscatter signal is generated by the interaction of the special standard patterns on the workpiece and the overwriting particle beam, and this signal is analyzed to identify and diagnose errors caused by the charged particle beam tool. The standard pattern may be formed using the same tool in its fully qualified state, and subsequent overlay tests may be conducted to identify changes in the state of that same tool.

21 Claims, 5 Drawing Sheets

CHARGED PARTICLE SYSTEM ERROR DIAGNOSIS

BACKGROUND OF THE INVENTION

1. Field of the Invention

This invention relates to charged particle beam systems and more specifically relates to charged particle lithography tools for semiconductor manufacturing.

2. Description of the Related Art

Charged particle beam lithography is a well-known process for patterning in the fabrication of semiconductor integrated circuits by "direct writing". This form of lithography is also used for patterning in the fabrication of photolithography masks. Charged particle beam lithographic tools typically include a beam source, beam steering and forming elements, a stage for a semiconductor wafer or mask blank (the workpiece), and a mechanism to move the stage with respect to the beam. For electron beam lithography, the beam source is an electron source and the beam steering and forming elements are an electron optical column. One commercially available electron beam lithography system is the Etec Systems, Inc. MEBES® ("Manufacturing Electron Beam Exposure System"). For focused ion beam lithography, the beam source is an ion source and the beam steering and forming elements are ion deflection and focusing elements.

Two common approaches to writing in an electron beam lithography system are referred to as "raster-scan" and "vector-scan". In raster scanning, an electron beam is scanned back and forth across the surface of the workpiece. The beam is turned on and off at appropriate times to create the desired pattern in an electron sensitive resist layer. The length of the scan distance on the substrate workpiece is typically limited to about 500 micrometers. To create patterns over large areas, the stage holding the workpiece is continuously moved. Both the beam scanning and the stage movement can introduce errors affecting the quality of the exposed patterns.

A vector scan electron beam lithography system operates in much the same way except that the beam is deflected only to positions at which pattern elements are to be exposed. The individual pattern elements are often written in raster fashion. During writing, the stage is generally stationary, and writing takes place over only a limited field, typically square in shape. Once the writing of the field is completed, the stage is moved to a new location, and another field written. Frequently, vector scan uses a variable shaped beam, which is a beam capable of having a different plan view size and/or shape each exposure. The pattern is then composed from these variable shapes. A shaped beam is capable of exposing multiple pixel sites simultaneously instead of one pixel site at a time, as in a raster scan strategy.

The tuning, diagnosis, and qualification of electron beam lithography systems is typically a lengthy process involving the writing and observation of a pattern of test patterns (features) on a workpiece. From these test patterns, placement errors can be identified, which assists in specifying setup parameters and diagnosing problems. In one exemplary process called MARKIT®, a pattern, typically a symmetric array of crosses, is written onto the workpiece. The workpiece is then rotated and the locations of the marks after development are measured. This allows detection of deviations from symmetry induced by the machine. From these measurements, a map of deviations from intended positions is produced, and analysis of this map allows problems to be diagnosed. One cycle of the procedure may take from hours to days to complete, so the time required for a feedback loop of diagnosis, repair, verification, and qualification can seriously impact a manufacturing facility's productivity.

In addition to the time required for these prior art techniques, there are various other disadvantages as well. First, the number of usable marks is limited, so marks tend to be large and widely spaced on the workpiece. Disturbances with a high spatial frequency may be overlooked during the inspection process because of the limited coverage of the test patterns. In addition, some periodic effects may be masked by the periodicity of the test patterns or by drift during measurement. Measurement precision should be in the range of approximately 10 nm, so there is often substantial scatter in the data. It may also be difficult to interpret temporal behavior from its consequences in the space domain due to aliasing and sampling effects. Finally, using this technique, it can be difficult to isolate error sources, particularly those that have their origin in asynchronous beam or stage vibrations.

U.S. Pat. No. 5,808,731 to Joseph P. Kirk describes a system and method for visually determining the performance of a photolithography system. Using this method, two patterns having different spatial frequencies are formed onto a workpiece. Each of these patterns individually include features small enough to make them difficult to optically resolve when using light in the visible regions. Therefore, in order to inspect the patterns, a scanning electron microscope (SEM) or similar inspection tool must be used to resolve such fine features. However, when the two patterns are overlaid, they combine to form a pattern in the resist that exhibits Moire beats. The Moire beat spatial frequency of the resulting pattern is significantly lower than the two individual spatial frequencies used, and thus can be visually inspected using light in the visible regions. Although Kirk teaches a method which enables the inspection of very fine features, it requires two lithography processes (including exposure and development), which results in significant delays, as described above. It also requires a second instrument (SEM).

"Beam-on-edge" techniques have also been used to detect displacement errors in electron beam lithography tools. A Gaussian or shaped beam is directed onto a special test transmission grid, and the current passing by the edge is detected. If the beam is directed such that half of the beam is occluded by the edge, then the transmitted current detected is one half of the total beam current, $I_0$. If the beam or stage experiences unwanted motion or placement error, then the error signal, $I_e=\Delta I/I_0$, is proportional to the placement error amplitude divided by the beam size ($\Delta x/x$ or $\Delta y/y$). Because the beam is comparable to the expected size of errors, the error signal for very small motions is a substantial fraction of the total current.

A disadvantage of current "beam-on-edge" methods is that they require a transmission grid/detector and a stationary stage. Thus, these methods cannot be used to measure accuracy while the beam or stage are moving. They also cannot be used on the workpiece itself because the electron beam cannot pass through to the transmission detector.

Accordingly, an improved system for calibrating and troubleshooting charged particle beam lithography equipment is needed. In particular, it would be desirable to have a system which decreases the cycle time for testing and analyzing, and which can be used to diagnose tools during their normal writing operations.

SUMMARY OF THE INVENTION

In accordance with the present invention, a method for diagnosing errors in a charged particle beam system comprises patterning a workpiece using a charged particle beam to expose a test pattern having a plurality of features, processing the pattern, directing a charged particle beam at said workpiece in an overlay pattern using a similar exposure sequence, receiving a signal generated by an interaction of said workpiece and said charged particle beam, and analyzing said signal.

In accordance with another aspect of the present invention, a method for diagnosing errors in a charged particle beam system comprises patterning a workpiece with a test pattern using a charged particle beam tool, directing a first charged particle beam from said charged particle beam tool at said workpiece in an overlay pattern, receiving a first signal generated by an interaction of said workpiece and said charged particle beam, and recording said first signal. Then, a second charged particle beam is directed from said charged particle beam tool at said workpiece in said test pattern. A second signal generated by an interaction of said workpiece and said charged particle beam is received and this second signal is compared with the first signal.

In accordance with yet another aspect of the present invention, a charged particle beam system comprises a charged particle beam source for providing a charged particle beam, a stage, a workpiece provided on said stage, said workpiece being patterned with a first test checkerboard pattern of repeating square features, a charged particle beam column for directing said charged particle beam onto said workpiece, and a backscatter detector for detecting a signal generated by an interaction of said charged particle beam and an edge of each of said features in said test pattern.

In accordance with another aspect of the present invention, a standard pattern substrate for testing a charged particle beam tool comprises a substrate having an upper surface, a coordinate system defined by an x-direction and a y-direction orthogonal to said x-direction, said x-direction and said y-direction defining a plane parallel to said upper surface of said substrate, and a plurality of metallic features patterned on said upper surface of said substrate, each of said metallic features having a first edge parallel to said x-direction and a second edge parallel to said y-direction.

BRIEF DESCRIPTION OF THE DRAWINGS

The present invention may be better understood, and its numerous objects, features, and advantages made apparent to those skilled in the art by referencing the accompanying drawings.

FIG. 1b is a depiction of a backscatter signal generated by the scanning of the feature in FIG. 1a.

FIG. 2b illustrates an enlarged portion of the view shown in FIG. 2a.

FIG. 3b is a depiction of a backscatter signal generated by the scanning of the standard pattern in FIG. 3a.

FIG. 4b is a depiction of a backscatter signal generated by the scanning of the standard pattern in FIG. 4a.

The use of the same reference symbols in different drawings indicates similar or identical items.

DETAILED DESCRIPTION

In accordance with the present invention, a "beam-on-edge" technique is used to diagnose errors in a charged particle beam system using a standard test pattern on a substrate (workpiece) that is overwritten using one or more similar overlay patterns. The edges of the features on the standard pattern are used to determine beam displacements.

Figure 1A:
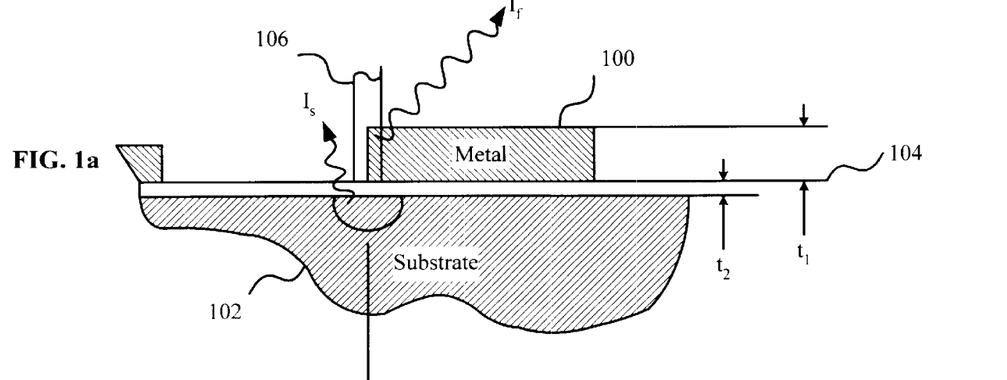
FIG. 1a is a cross-section of a special test feature formed on a substrate as part of a standard pattern used in accordance with the present invention.

FIG. 1a shows a cross-section of a test feature 100 formed on a substrate 102, with a thin electrically conducting layer 104 deposited therebetween. Feature 100 is, for example, a 0.25–0.5 $\mu$m thick layer of tungsten, gold, or platinum, and is one of a plurality of features forming a standard test pattern on substrate 102. In order to more closely simulate actual lithographic writing, substrate 102 itself may be identical to the type of substrate (wafer or mask blank) expected to be exposed by the tool being tested. Unlike prior art "beam-on-edge" methods, solid substrates, such as glass masks, silicon wafers, and X-ray masks, can be used because the invention does not require that a transmission grid be used to detect transmitted electrons. Instead, a backscatter detector 214 (FIG. 2c) is used to detect electrons which are backscattered from the location where charged particle beam 106 impacts the workpiece.

When exposed by a charged particle beam, many substrate types create a large backscatter signal originating from scattering within the substrate. Such a signal may interfere with the precise detection and resolution of the edge of feature 100. A conducting layer 104 deposited between feature 100 and substrate 102 may be used to reduce this undesirable backscattering from substrate 102. In one embodiment, conducting layer 104 is a 0.1 $\mu$m thick layer of, for example, chromium or gold. Conducting layer 104 inhibits the transmission of backscattered electrons passing upwards from substrate 102, thereby ensuring that the majority of the detected backscatter signal, $I_d$, originates with primary charged particle collisions on the surface of feature 100 and conducting layer 104, rather than from substrate scattering.

Figure 1B:
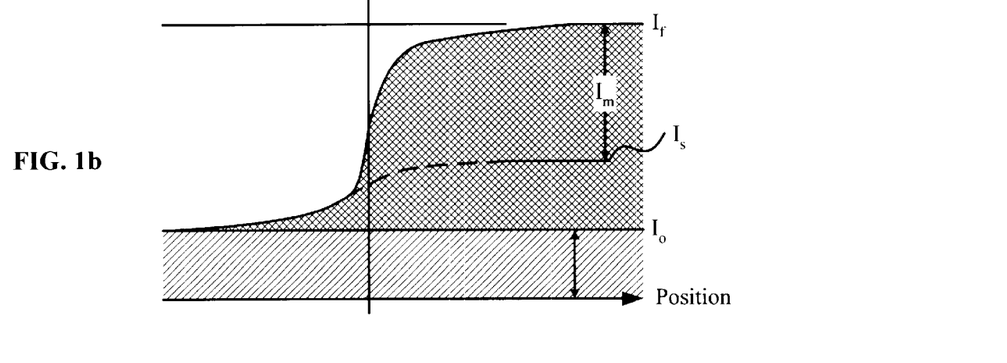

FIG. 1b illustrates an exemplary waveform of signal versus position as a beam 106 is scanned over feature 100 in FIG. 1a. When beam 106 is located over feature 100, a large backscatter signal, $I_f$, from the high atomic number material is produced. When beam 106 is located over substrate 102 and conducting layer 104, a weaker signal, $I_o$, is produced. Superimposed in the waveform is a blurred image, $I_s$, resulting from multiple scattering in substrate 102. With proper selection of thicknesses $t_1$ (feature 100) and $t_2$ (conducting layer 104), signal $I_s$ may be reduced, creating a high contrast signal similar to that from a transmission detector, enabling precise determination of the location of feature 100 relative to beam 106.

Figure 2A:
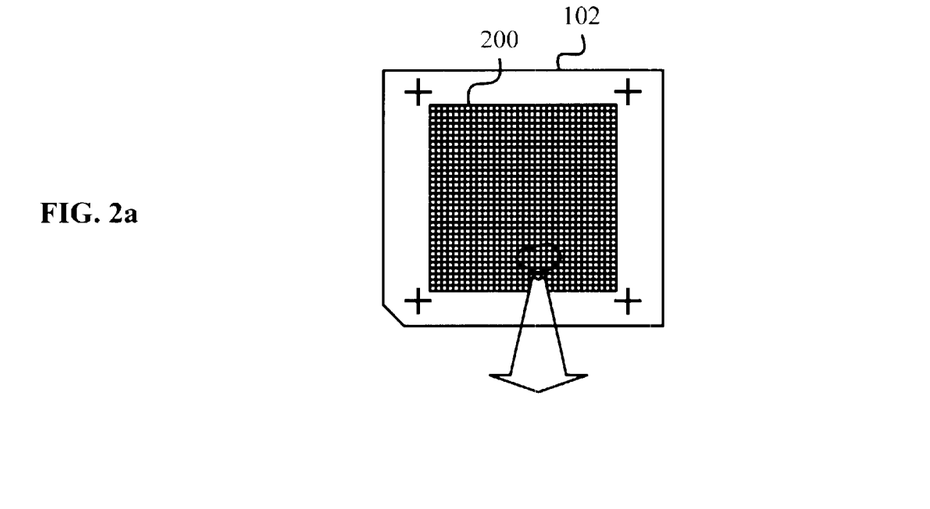
FIG. 2a illustrates in a plan view a substrate having a standard pattern in accordance with the present invention.
Figure 2B:
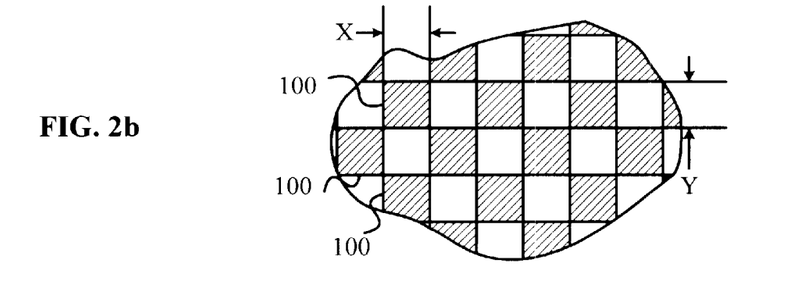

FIG. 2a is a top view of substrate 102, having standard pattern 200 formed thereupon. FIG. 2b shows an enlarged view of a portion of standard pattern 200, which is composed of a checkerboard array of square features 100, each feature 100 having an x-direction width and y-direction length of approximately 0.5 $\mu$m, and a unit cell period of 1.0 $\mu$m. This standard pattern substrate 102 is written once, qualified and characterized by standard metrology and inspection methods, and may be used repeatedly in different machines for real-time qualification and diagnosis, as will be described in greater detail below.

Figure 3A:
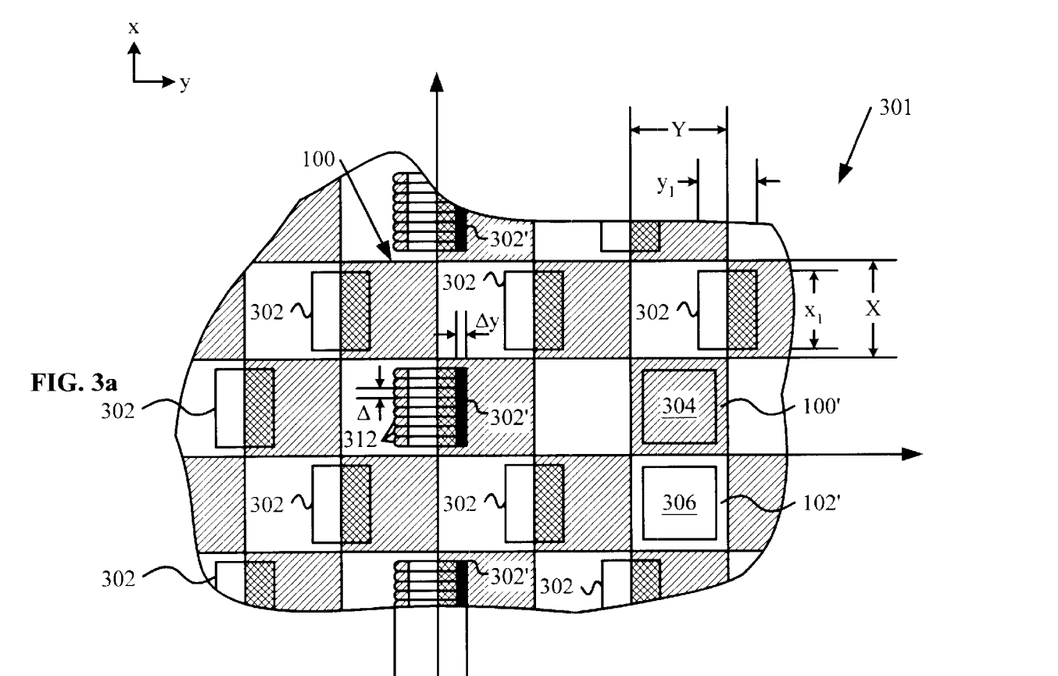
FIG. 3a shows an overlay pattern scanned on a standard pattern in accordance with the present invention.

Substrate 102 is placed onto the stage of the lithography tool to be tested and is registered with respect to the writing beam using standard methods that image standard fiducial marks, such as cross-shaped marks. The tool then exposes (using raster or vector scanning) an overlay pattern 301 onto substrate 102, as illustrated in FIG. 3a. Overlay pattern 301 includes a plurality of regions 302 arranged to correspond with the standard pattern 200 of features 100. Each overlay region 302 is located such that the writing beam during writing extends over one edge of each of the features 100, half of region 302 being above a feature 100, and half being above substrate 102.

Figure 2C:
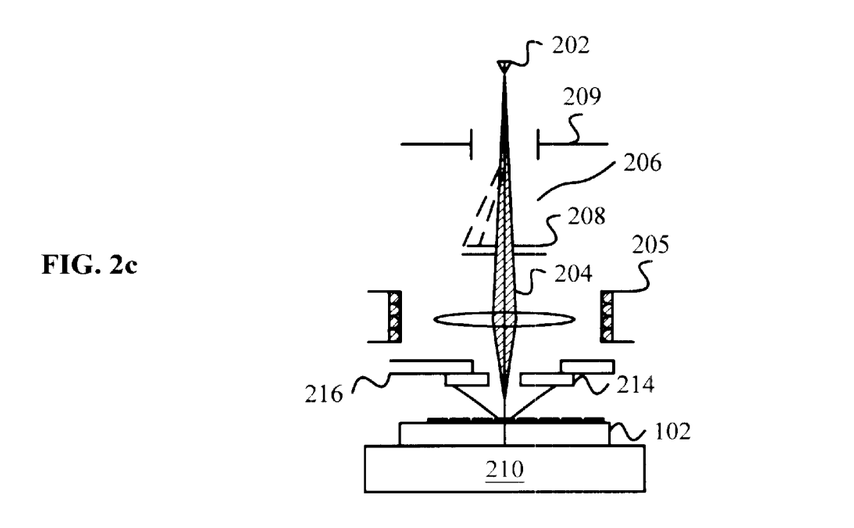
FIG. 2c illustrates a charged particle beam system in accordance with the present invention.

FIG. 2c shows, in simplified form, a charged particle beam system 206 having an electron beam source 202 which generates an electron beam 204. Beam 204 passes through aperture 208, scanned by deflectors 205 on the upper surface of standard pattern substrate 102, which is mounted onto movable stage 210. One or more backscatter electron detector diodes 214 are mounted onto plate 216. The beam is turned on and off by blanker 209 to expose a pattern.

FIG. 3a shows one possible substrate test pattern shown in FIG. 2, and a superimposed overlay test pattern written during a test. In FIG. 3a, the x-direction is the direction in which the stage supporting substrate 102 is moved during writing, and the y-direction is the direction in which the particle beam scans. In this example, overlay regions 302 having dimensions of $x_1$=0.45 μm and $y_1$=0.20 μm are arranged such that each region 302 overlaps one edge of each feature 100. In one embodiment, only one edge of each feature 100 is used, so that variations in the size of features 100 do not influence the position measurements. Therefore, only the period of features 100 is important.

As an example, a shaped beam vector scan system might generate individual 0.25 μm×2 μm rectangular flashes stepped on a 1.0 μm period to form overlay regions 302. In an equivalent raster scan embodiment with a 0.05 μm address, the corresponding pattern would be created with a string of five exposed pixels followed by 15 blanked pixels. After 40 scans, the phase would be shifted by 10 pixels so that the edges of the next row of checkerboard features are exposed. (These parameters, as are other numerical values provided here, are exemplary and not limiting).

Figure 3B:
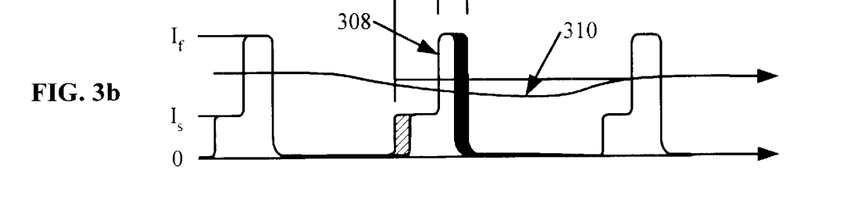

The output signal of the backscatter detector is a pulse whose amplitude is proportional to the degree of overlap between the beam and feature 100. Thus, amptitude measures position with respect to the edge of feature 100. This output signal waveform is shown in FIG. 3b aligned with corresponding portions of FIG. 3a. When standard pattern 200 is completely aligned with overlay pattern 301, the unblanked portion of the video signal gives full backscatter yield, $I_f$, for that portion of the figure completely overlying feature 100, a lower yield, $I_s$, for that portion above the exposed substrate 102, and a zero yield when the beam is blanked. $I_f$ and $I_s$ can be determined by recording the backscatter current of reference regions 304, 306, respectively. Reference region 304 is located completely within the borders of feature 100' and reference region 306 is located completely within the borders of a featureless portion 102' of substrate 102. Backscatter measurements taken in regions 304, 306 provide reference values for interpreting the signals received during scanning of overlay regions 302.

The pulse waveform 308 shown in FIG. 3b is integrated using a conventional square response filter to exclude frequencies higher than the 1.0 μm pattern period of overlay regions 302. Using a 160 MHz raster-scan MEBES system from Etec Systems, Inc., this filter would eliminate frequencies higher than approximately 4 MHz. The upper limit would be approximately 10 MHz for a vector scan tool having a 100 nsec flash cycle. The amplitude of the integrated signal 310 reflects the overlap of the writing beam with the x-direction edge of standard pattern 200. The amplitude increases or decreases according to the relationship of the beam with the edge. This charge integrated video signal 310 may be further filtered, averaged, or spectrum analyzed to emphasize various frequency ranges, ranging from DC to 4 MHz.

In FIG. 3b, $I_f$ (in units of nA) is the detected backscatter signal resulting from the beam striking feature 100, and $I_s$ is the detected backscatter signal resulting from the beam striking the substrate 102. Where $y_1$ (in μm) is the width of overlay region 302, and $Y_1$ is the width of feature 100, then the filtered charge integrated video signal, $I_i$ is calculated as follows:

$$I_i = I_f(y_1/2Y_1), \text{ when the beam is fully on feature 100;}$$

and $$I_i = I_s(y_1/2Y_1), \text{ when the beam is fully on substrate 102.}$$

When the overlay pattern is precisely aligned with standard pattern 200, each overlay region 302 has 50% of its area over a feature 100 and 50% of its area over other portions of substrate 102. Thus, the mean signal amplitude, $I_m$, is calculated as follows:

$$I_m = (I_f - I_s)(y_1/4Y_1).$$

When the overlay regions 302 are not precisely aligned with features 100 of the standard pattern 200, the backscatter signal reflects this misalignment. In FIG. 3a, misaligned regions 302' are displaced in the y-direction from their expected location by a distance Δy, which causes a signal change, ΔI, as follows:

$$\Delta I = (I_f - I_s)\left(\frac{y_1}{2Y}\right)\left(\frac{\Delta y}{y_1}\right) = (I_f - I_s)\left(\frac{\Delta y}{2Y}\right).$$

Therefore, the percentage of signal modulation, M%, is as follows:

$$M\% = \left[\frac{2(I_f - I_s)}{(I_f + I_s)}\right]\left(\frac{\Delta y}{y_1}\right)\%$$

The percentage of signal modulation, M%, is the signal contrast times the ratio of error to test shape size. This scheme accurately simulates the static "beam-on-edge", but does not require a transmission grid and can be performed during actual writing using an overlay pattern with a moving stage.

Figure 4A:
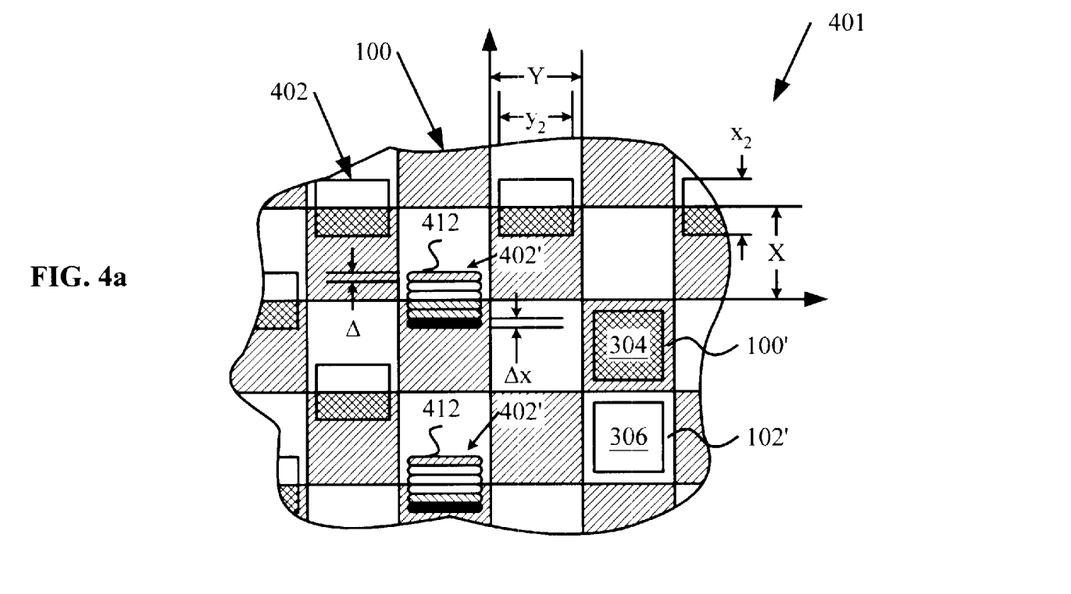
FIG. 4a shows a second overlay pattern scanned on the standard pattern in accordance with the present invention.

FIG. 4a illustrates in a plan view a second overlay pattern 401 used to detect positional errors in a direction perpendicular to the direction of scanning (the y-direction). The associated test process uses the same substrate 102 as described above with standard pattern 200, which enables substrate 102 to be used for measurements both parallel and perpendicular to the scan direction. The test involves writing an overlay pattern 401 which includes an array of overlay regions 402 having similar dimensions ($x_2$=0.20 μm, $y_2$=0.45 μm) as overlay regions 302, but arranged such that they overlie an edge of each feature 100 perpendicular to the edge used in FIG. 3a. Using a raster scan system, each overlay region 402 is written as a plurality of scan lines 412, each scan line 412 being parallel to the y-direction edge of each feature 100 and having a width Δ corresponding to the width of the beam.

Figure 4B:
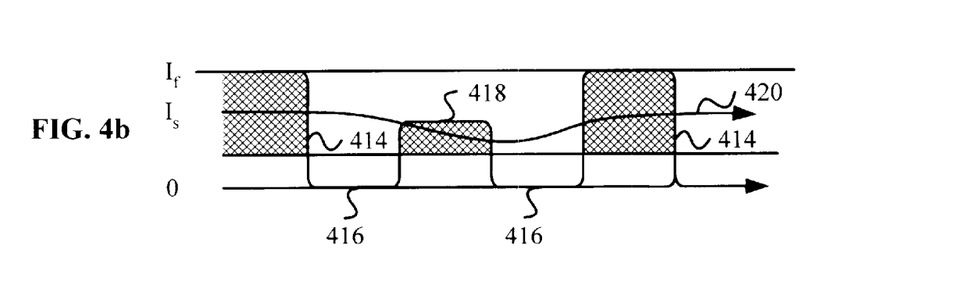

FIG. 4b illustrates the resulting backscatter signal detected when the beam overlaps the edge of features 100. Peak amplitude signals 414 correspond to the backscatter signals received when the beam overlaps a portion of a feature 100. The signal level for peak signals 414 are approximately equal to the maximum backscatter signal, $I_f$, received when the particle beam is incident only on the metal in feature 100. When the beam is blanked off in region 416, the signal is zero. As above, this maximum signal, $I_f$, can be determined by scanning a reference region 304 completely within the borders of the a feature 100, and the signal corresponding to the backscatter received while scanning the substrate is determined by scanning reference region 306. When the scanned beam overlays a horizontal edge, the signal levels for signals 418 are lower than $I_f$, and the resulting detected signal is therefore reduced by the amount of the beam area which is overlapping substrate 102.

Misaligned regions 402' are offset in the x-direction by a distance Δx as shown. Peak 418 corresponds to misaligned region 402', and the backscatter signal value is less than the values for peaks 414 by an amount corresponding to the positional error, Δx. Because scan line 412 is parallel to the feature edge, the modulation of the detected backscatter signal is proportional to Δx/Δ, instead of Δy/y₁, as was the case in FIG. 3a, where the scan line 312 is perpendicular to the measured edge. Integrated signal 420 reflects the modulation in the detected backscatter signal.

Providing a high density of features 100 in the standard pattern 200 enables very sensitive measurements because the "beam on" duty cycle is favorable (i.e., many electrons are used to make the measurement). In a MEBES IV tool by Etec Systems, Inc., operating at J=500 A/cm² with a flash time of 6.25 nsec. and a beam diameter of 0.08 μm, the beam current is 25 nA, and there are approximately 1000 incident electrons per pixel in area Δ². Assuming a 50% backscatter yield for reference region 304 above feature 100 ($I_f$≈12.5 nA or 500 electrons/pixel) and a 10% backscatter yield for reference region 306 above substrate 102' ($I_s$≈1.25 nA or 50 electrons/pixel), the mean signal current would be 3.7% of the total beam current ($I_{mean}$≈1.87 nA or 73 electrons/pixel). From this we estimate a signal-to-noise ratio of about 20:1 for a video signal of 4 MHz bandwidth.

It is desirable to reduce the effect of noise on the signal data obtained during the testing in order to emphasize the distortions caused during writing. Digital oscilloscopes and spectrum analyzers can be used to average the waveforms created over many features 100 in substrate 102 to remove noise. Digital oscilloscopes allow a rolling average over the individual waveforms, and spectrum analyzers can average the data set over the entire duration of testing.

In accordance with another aspect of the present invention, the backscatter detection signals are analyzed to determine and diagnose the particle beam tool's performance. The signals received by the detector are displayed as a video signal in the time sequence that overlay patterns 301, 401 are written. The conversion of the signal data from the time domain to the positional domain depends upon the writing strategy, i.e., the sequence order in which overlay regions 302, 402 are exposed. Periodic distortions and asynchronous vibrations will have different consequences upon the overlay pattern. Any variation in the integrated backscatter signal data away from its mean value implies a placement error.

Figure 5A:
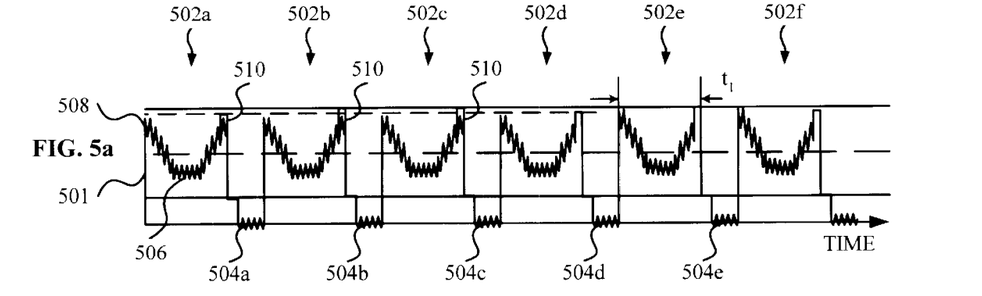
FIGS. 5a–5d depict backscatter waveforms detected in accordance with the present invention.

FIGS. 5a–5d illustrate waveforms characteristic of various kinds of problems encountered with a raster scan system and diagnosed as described herein. FIG. 5a shows a waveform 501 obtained when there is a distortion in the y-direction of Δy, as shown in FIG. 3a. The width of each rise 502 corresponds to the time, $t_1$, of each scan line 312. The distortion 506 occurs with a frequency equal to the frequency of the beam scan, so each scan line 312 experiences the same distortion.

Figure 5B:
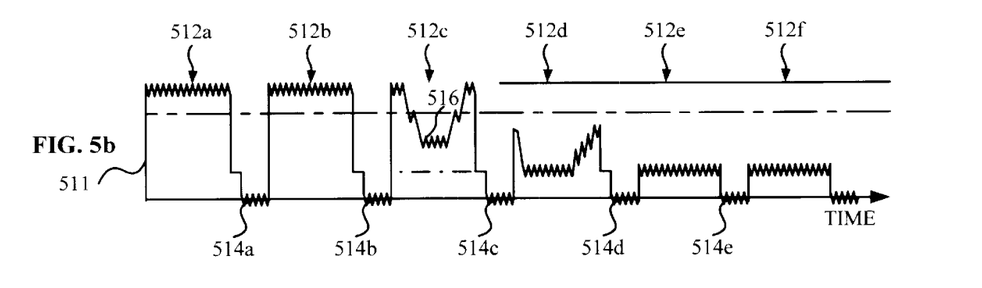

FIG. 5b shows a waveform 511, which corresponds to a distortion, Δx, occurring in the x-direction, as shown in FIG. 4a. The distortion 516 appears only in the scan line 412 intersecting the edge of the feature 100, which corresponds to rise 512c. Each rise 512 is separated from the subsequent rise 512 by a blank signal portion 514a–514e. If butting errors existed, these would be evidenced by a discontinuity in one of the blank signal portions 514a–514e.

Figure 5C:
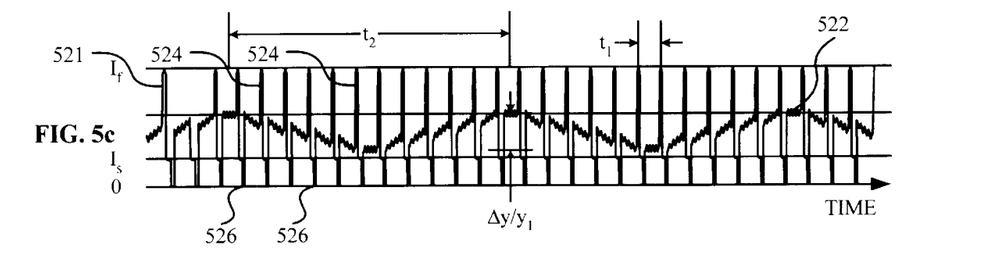
Figure 5D:
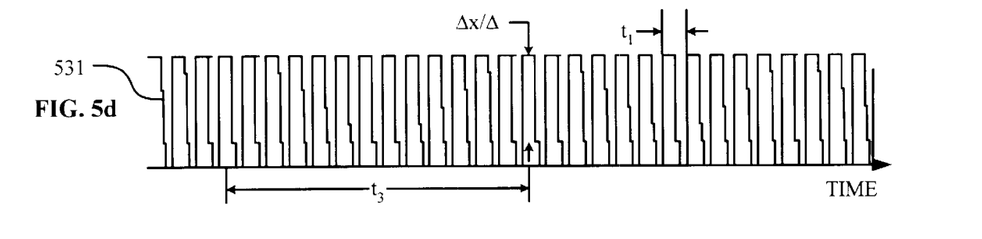

FIGS. 5c–5d show waveforms 521, 531, which illustrate exemplary signatures caused by an asynchronous vibration or electromagnetic interference occurring at a frequency much lower than the periodicity of features 100 in standard pattern 200. FIG. 5c shows waveform 521, which occurs when there is an interference causing errors in the y-direction. Waveform 521 includes peaks 524, valleys 526, and a central curve 522, which is the darker region defined by the signal obtained at the intersections with the edge of the features 100. Central curve 522 experiences a distortion of Δy/y₁, which has a period of $t_2$ much larger than the period ($t_1$=30 μsec) of the scanning of features 100 in standard pattern 200. Such errors may be caused by, for example, deflection distortion in the scan direction due to mechanical vibrations or noise in deflection or alignment electronics. FIG. 5d shows waveform 531, which is obtained when there is an interference causing errors in the x-direction. The distortion is proportional to Δx/Δ and has a period of $t_3$. This type of error may be caused by, for example, stage tracking errors or deflection distortion orthogonal to the scan axis due to mechanical vibrations or noise in deflection or alignment electronics. Other types of observable errors include distortions resulting from long term drift or sudden shifts in the beam or substrate position.

Diagnosis of vector scan tools can be performed similarly to the raster scan method described above. In one embodiment, the standard pattern is overwritten in the same sequence as it is normally written using electrostatically addressed subfields having a single shape stepped along serpentine or sawtooth trajectories. In this case, the waveforms associated with distortions in the x- and y-directions are interpreted the same way. Within each subfield, there will be repetitive waveforms associated with the time required to complete a scan line along one axis, and also with the time to complete an entire subfield. These waveforms will reflect subfield distortions. There would be another characteristic frequency for the distortion of the magnetically addressed steps between subfields associated with the time required to complete all the minor fields across a stripe on the substrate. Asynchronous disturbances and vibrations associated with stage motion would likely manifest as oscillations or peaks at lower frequencies. Different kinds of errors may be explored by composing vector scan writing patterns with different trajectories. The use of flashes in vector scan systems may make data interpretation easier than the interpretation needed for line scans in raster-based systems.

It is likely that the standard pattern substrate 102 will not be perfectly formed, because there are no perfect lithography machines available to create the pattern. Nevertheless, embodiments of the present invention can be used in conjunction with imperfect standard patterns 200. First, edge roughness defects may be averaged out by using a standard pattern 200 having a significantly large number of features 100 to be scanned.

Another method which may be used to improve the standard pattern substrate is to fabricate it using an insensitive resist and a multiple exposure voting technique involving several different exposure passes. Yet another method is to fabricate the standard pattern substrate in an optical stepper from a demagnified reticle. This would demagnify the placement errors in the fabrication lithographic tool, which might otherwise be difficult to distinguish from the placement errors in the tool being tested. Masks can also be independently qualified used standard metrology equipment that use a light beam and highly accurate interferometer as a measurement standard.

In another aspect of the present invention, the standard pattern substrate is fabricated using a fully qualified lithographic tool at the peak of its performance. Immediately after creation of the standard pattern substrate, the diagnosis tests described above are performed to obtain a standard data set for that tool. If the tool does not experience any degradation in performance, each time the diagnosis tests are performed, identical data sets will be obtained. However, if the subsequent tests produce different data sets, then the standard data set can be compared with the new data to produce a differential data set which identifies changes in the state of the machine from its fully qualified state. This subtractive technique using standard pattern substrates unique to each tool can be used to detect problems and requalify performance, even if the standard pattern substrates are imperfect. If the absolute accuracy of masks improves, a plurality of tools can be calibrated to a fixed metrology standard.

Although the invention has been described with reference to particular embodiments, the description is only an example of the invention's application and should not be taken as a limitation. For example, features on test patterns are not restricted to being rectangular in shape. In addition, even though much of the preceding discussion was directed to electron beam lithography tools, embodiments of the present invention are applicable to, for example, electron beam inspection, electron beam microscopy, ion beam lithography, and ion beam microscopy. Various other adaptations and combinations of features of the embodiments disclosed are within the scope of the invention as defined by the following claims.

I claim:

1. A method for diagnosing errors in a charged particle beam system, comprising the acts of:
   providing a workpiece patterned with a first test pattern having a plurality of features;
   directing a charged particle beam at said workpiece, said charged particle beam being directed at said workpiece in a manner defined by an overlay pattern, wherein said directing comprises periodically directing said charged particle beam along an edge of at least one of said plurality of features on the first test pattern;
   detecting a signal generated by an interaction of said workpiece and said charged particle beam; and
   analyzing said signal.

2. The method of claim 1, wherein said first test pattern defines a plurality of rectangular features in a periodic array.

3. The method of claim 1, wherein said overlay pattern comprises a plurality of regions, each of which overlays an edge of one of said plurality of features.

4. The method of claim 1, wherein said analyzing comprises determining a frequency spectrum of a modulation in said signal.

5. The method of claim 4, wherein said analyzing further comprises correlating the determined frequency spectrum with a spatial distortion in the overlay pattern characteristic of a performance deficiency in a system generating the overlay pattern.

6. The method of claim 4, wherein said analyzing further comprises viewing a representation of said determined frequency spectrum.

7. The method of claim 1, wherein said analyzing comprises viewing a representation of said detected signal.

8. The method of claim 1, wherein said directing comprises:
   directing an electron beam at said workpiece in said overlay pattern; and
   said detecting comprises detecting backscattered electrons.

9. The method of claim 8, wherein said detecting comprises using a backscattered electron detector.

10. A method for diagnosing errors in a charged particle beam tool, comprising the acts of:
    patterning a workpiece with a first test pattern using a charged particle beam tool;
    directing a first charged particle beam from said charged particle beam tool at said workpiece, said first charged particle beam being directed at said workpiece in a manner defined by an overlay pattern;
    detecting a first signal generated by an interaction of said workpiece and said charged particle beam;
    recording said first signal;
    directing a second charged particle beam from said charged particle beam tool at said workpiece in said first test pattern;
    detecting a second signal generated by an interaction of said workpiece and said charged particle beam; and
    comparing said second signal with said first signal.

11. The method of claim 10, wherein said patterning comprises patterning said workpiece with a plurality of rectangular features.

12. The method of claim 10, wherein:
    said directing said first charged particle beam comprises directing said first charged particle beam at said workpiece along an edge of at least one of said plurality of features; and
    said directing said second charged particle beam comprises directing said second charged particle beam at said workpiece along the edges of said plurality of features on said first test pattern.

13. The method of claim 10, wherein said overlay pattern comprises a plurality of regions, each of which overlays an edge of one of said plurality of features.

14. The method of claim 10, further comprising analyzing said first and second signals.

15. The method of claim 14, wherein said analyzing said first and second signals comprises determining a frequency spectrum of a modulation in said first signal and said second signal.

16. The method of claim 15, wherein said analyzing said first and second signals further comprises correlating the determined frequency spectrum with a spatial distortion in the overlay pattern that is characteristic of a performance deficiency in a system generating the overlay pattern.

17. The method of claim 14, wherein said analyzing said first and second signal comprises:
    viewing a representation of said first signal; and
    viewing a representation of said second signal.

18. The method of claim 17, wherein:

said viewing said representation of said first signal comprises viewing a representation of a frequency spectrum of said first signal; and viewing a representation of said second signal comprises viewing a representation of a frequency spectrum of said second signal.

19. The method of claim 10, wherein:

said directing said first charged particle beam comprises directing a first electron beam at said workpiece in said overlay pattern;

said detecting said first signal comprises detecting backscattered electrons generated by the interaction of said workpiece and said first electron beam;

said directing said second charged particle beam comprises directing a second electron beam at said workpiece in said overlay pattern to generate a second backscattered electron signal produced by the interaction of said workpiece and said second electron beam; and said detecting said second signal comprises detecting backscattered electrons generated by the interaction of said workpiece and said second electron beam.

20. The method of claim 19, wherein said detecting said first signal comprises using backscattered electron signal.

21. A charged particle beam system, comprising:

a charged particle beam source for providing a charged particle beam;

a stage;

a workpiece provided on said stage, said workpiece being patterned with a first test checkerboard pattern of repeating square features;

a charged particle beam column for directing said charged particle beam onto said workpiece, said charged particle beam being directed at said workpiece in a manner defined by an overlay pattern; and a backscatter detector for detecting a signal generated by an interaction of said charged particle beam and an edge of each of said features in said first test pattern.

* * * * *